(12) United States Patent
Wang et al.

(10) Patent No.: US 6,772,152 B2
(45) Date of Patent: Aug. 3, 2004

(54) SYSTEM AND METHOD FOR MINING PATTERNS FROM A DATASET

(75) Inventors: Wei Wang, White Plains, NY (US); Jiong Yang, White Plains, NY (US); Philip Shi-Lung Yu, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 290 days.

(21) Appl. No.: 09/814,512

(22) Filed: Mar. 22, 2001

(65) Prior Publication Data

US 2002/0161758 A1 Oct. 31, 2002

(51) Int. Cl.[7] .............................. G06F 17/30; G06K 9/62
(52) U.S. Cl. ........................................... 707/6; 382/225
(58) Field of Search ............................. 707/6; 382/228, 382/181, 224, 225

(56) References Cited

U.S. PATENT DOCUMENTS

| | | | | |
|---|---|---|---|---|
| 5,748,769 A | * | 5/1998 | Nishimura et al. | 382/159 |
| 5,825,925 A | * | 10/1998 | Baird et al. | 382/225 |
| 5,940,535 A | * | 8/1999 | Huang | 382/201 |
| 6,001,562 A | * | 12/1999 | Milosavljevic | 435/6 |
| 6,289,328 B2 | * | 9/2001 | Shaffer | 706/20 |
| 6,353,679 B1 | * | 3/2002 | Cham et al. | 382/228 |
| 6,400,853 B1 | * | 6/2002 | Shiiyama | 382/305 |
| 6,507,843 B1 | * | 1/2003 | Dong et al. | 707/6 |

OTHER PUBLICATIONS

Liuni et al "A new parallel algorithm for computation of statistically significant patterns in DNA sequences", IEEE 1993, pp. 605–612.*
Dimauro et al "Classification of ambiguous patterns", IEEE 1992, pp. 520–524.*
Zhang et al "Exploring constraints to efficiently mine emerging patterns from large high–dimensional datasets", ACM 2000, pp. 310–314.*
Han et al "Mining frequent patterns without candidate generation", ACM 2000, pp. 1–12.*
Guha et al "CURE: an efficient clustering algorithm for large databases", ACM 1998, pp. 73–84.*

* cited by examiner

*Primary Examiner*—Uyen Le
(74) *Attorney, Agent, or Firm*—F. Chau & Associates, LLC

(57) ABSTRACT

A system and method are provided for discovering significant patterns from a list of records in a dataset. Each record includes a set of items, and each significant pattern includes a subset of items such that a significance of the pattern exceeds a significance level. A significance is computed for each item in the list of records to determine significant items. The records are randomly sampled to select a sample portion of the records. Ambiguous patterns are identified against the sample portion of the records and verified against the entire list of records in the dataset.

25 Claims, 6 Drawing Sheets

SYSTEM AND METHOD FOR MINING PATTERNS FROM A DATASET

BACKGROUND OF THE INVENTION

1. Field of the Invention

The present invention relates to data mining, and more particularly to mining long patterns in a large data set.

2. Description of the Related Art

Finding patterns in data has been an important but difficult task in many industries. Pattern discovery is of increasing importance in many applications including but not limited to biology study, consumer behavior analysis, system performance analysis, etc. A pattern discovery problem may be formulated as follows. Let $D=\{d_1, d_2, \ldots, d_m\}$ be a set of literals. A pattern P is a subset of items in D. A pattern consisting of k items is usually referred to as a k-pattern. Given two patterns $P_1$ and $P_2$, $P_1$ is called a sub-pattern of $P_2$ if $P_1$ can be generated by removing some item(s) from $P_2$. In such a case, $P_2$ is called a super-pattern of $P_1$. For example, $d_1d_2$ is a sub-pattern of $d_1d_2d_3$. The sub-pattern/super-pattern relationship defines a lattice among all patterns. Given a data set T and a pattern P, let s(P) denote the significance of P in T. The goal is to discover all patterns $\{P|s(P) \geq \text{min\_sig}\}$, where min_sig is a user-specified threshold. A pattern is also referred to as a significant pattern P if $s(P) \geq \text{min\_sig}$. Otherwise, it is called an insignificant pattern. Serious challenges are posed to the design of a mining algorithm because the data set is typically very large (i.e., only a small fraction of the entire data set can be held in memory at once) and patterns may be substantially long (i.e., including a large number of items or events). Even with the help of the well-known Apriori property, the traditional level-wise algorithm becomes very slow.

The Apriori property states that the significance of a pattern is always less than or equal to the significance of any of its sub-patterns. This leads to a level-wise iterative evaluation of significance of patterns: at the kth level, all candidate k-patterns are evaluated via a scan of the data and the set of significant k-patterns are identified and used to generate candidate (k+1)-patterns according to the Apriori property. The process ends when no new candidate pattern can be generated. For example, if $d_1d_2$, $d_1d_3$, $d_1d_4$, $d_1d_5$, $\ldots$, are significant 2-patterns, then $d_1d_2d_3$, $d_1d_2d_4$, $d_1d_3d_4$, $d_1d_2d_5$, $d_1d_3d_5$, $d_1d_4d_5$, $\ldots$, are candidate 3-patterns in the level-wise search. It is easy to see that k scans of the data are required if a significant pattern may consist of up to is k items.

Some effort has been made to further improve performance of finding significant patterns, especially to address the inefficiency incurred by a relatively large value of k. MAXMINER (available commercially from IBM) introduced a "look-ahead" strategy in addition to the traditional level-wise approach. During the generation of candidate (k+1)-patterns from significant k-patterns, some additional candidate patterns of higher levels are also generated and evaluated together with the candidate (k+1)-patterns. In the above example, $d_1d_2d_3d_4d_5$ will also be generated as a candidate pattern. Note that if $d_1d_2d_3d_4d_5$ is significant, then any of its sub-patterns is significant without further test. Though this approach can reduce the number of scans of the data to some extent, such reduction may be insufficient and not guaranteed in many cases, especially when significant patterns include a large number of items. As a result, the MAXMINER is only suitable to mining patterns that include items in the range of dozens.

Another approach includes the use of sampling. In this approach, a set of samples are first gathered, and the significant patterns in the sample data are computed. F represents the set of significant patterns in the sample data and their immediate super-patterns. The significances of patterns in F are then computed based on the entire dataset and serve as the (advanced) starting position of a level-wise search that eventually identifies all significant patterns. This strategy is efficient if the number of significant patterns that fail to be recognized from the sample is small, which is typically the case under the assumption of a reasonably large sample size and a relatively short pattern length. However, the number of candidate patterns may be considerably large and may not fit into the main memory all at once. In turn, multiple scans of the entire data set may be required.

Therefore, a need exists for a system and method which mines patterns from a large data set. A further need exists for an efficient method which mines data from a large data set only a few scans.

SUMMARY OF THE INVENTION

A system and method are provided for discovering significant patterns from a list of records in a dataset. Each record includes a set of items, and each significant pattern includes a subset of items such that a significance of the pattern exceeds a significance level. A significance is computed for each item in the list of records to determine significant items. The records are randomly sampled to select a sample portion of the records. Ambiguous patterns are identified against the sample portion of the records and verified against the entire list of records in the dataset. This provides an efficient method for data mining.

In other embodiments, a significance computation may be performed for each item in a single scan of the list of records. The step of sampling the records may include choosing a sample size according to a size of available memory space for storing sampled records.

The step of identifying ambiguous patterns may include an iterative loop, wherein a kth iteration identifies all ambiguous k-patterns. The method may include the steps of generating candidate k-patterns, computing the significance of each candidate k-pattern in the sample portion and labeling candidate k-patterns as significant, ambiguous, or insignificant according to the significance of each candidate k-pattern in the sample portion.

A Chernoff Bound may be used to label candidate k-patterns. A domain of each candidate k-pattern may be computed from the significance of each involved item from the list of records of the dataset. Ambiguous patterns may be verified against the entire list of records. This may include pruning ambiguous patterns by employing an ordered pruning method. The ambiguous patterns may be pruned to fit together in a same memory space.

The ordered pruning method may include an iterative process, wherein each iteration may include computing a set of halfway patterns in a space of ambiguous patterns, determining significances of the halfway patterns in the entire list of records of the dataset and reducing the space of ambiguous patterns.

These and other objects, features and advantages of the present invention will become apparent from the following detailed description of illustrative embodiments thereof, which is to be read in connection with the accompanying drawings.

BRIEF DESCRIPTION OF DRAWINGS

The invention will be described in detail in the following description of preferred embodiments with reference to the following figures wherein.

DETAILED DESCRIPTION OF PREFERRED EMBODIMENTS

Figure 1:
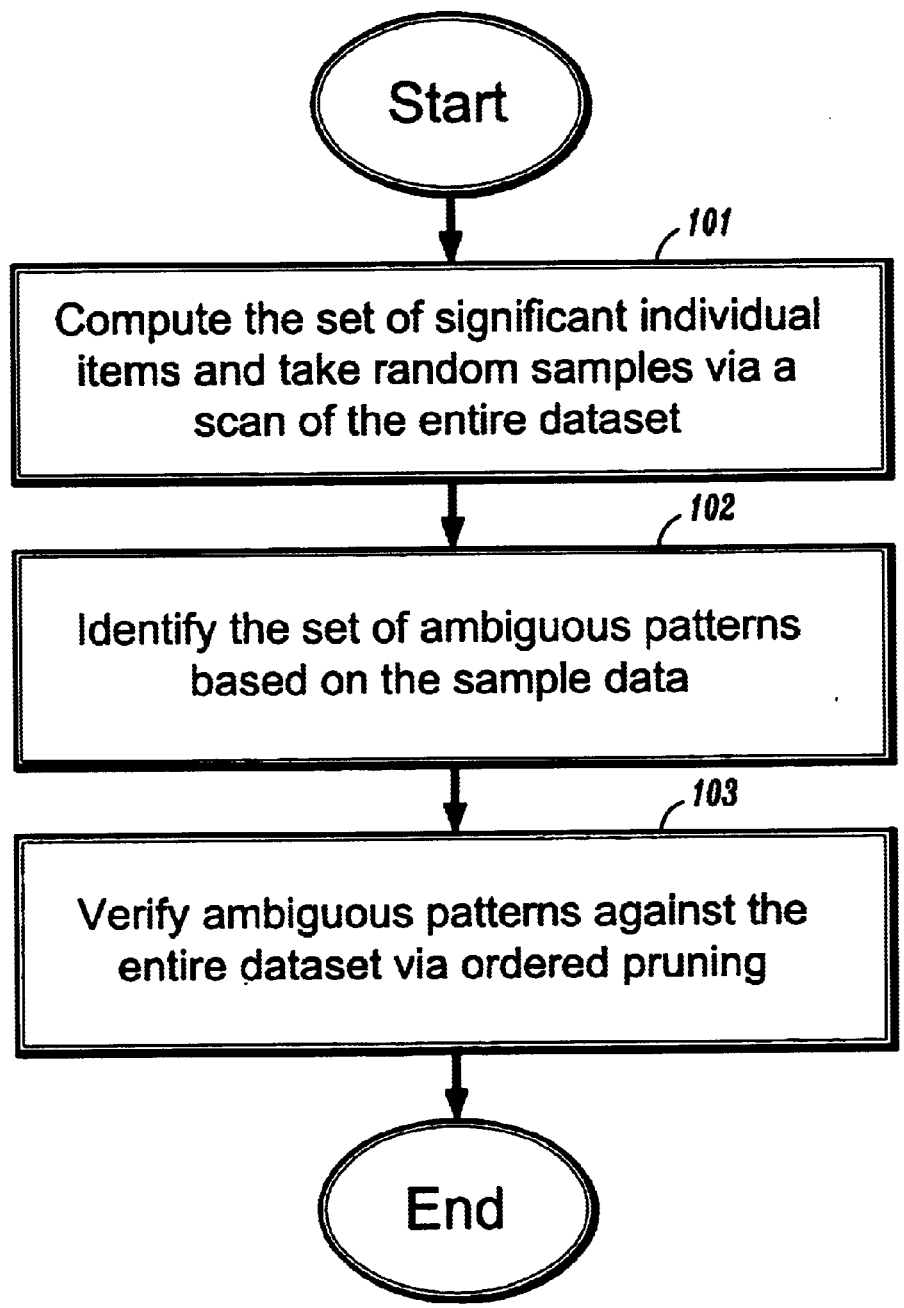
FIG. 1 is a block/flow diagram depicting a system/method of mining significant patterns that meet a user-specified threshold min_sig in accordance with the present invention.

The present invention provides an efficient system and method for mining patterns that may include thousands of items in a few scans of the data. According to the present invention, a novel sampling-based approach is devised. Given a random sample of the data, a Chernoff Bound, or other statistical modifier, is used to estimate the set of patterns whose significances in the sample are very close to the threshold so that there is no sufficient statistical confidence to tell whether the pattern would be significant or not in the entire dataset.

In one embodiments, let Y be a random variable whose domain is R. The domain of a random variable is defined as the difference between the maximum possible value and the minimum possible value of the random variable. For example, in the context of the present invention, the significance is usually a number between 0 and 1, and R is less than or equal to 1. Suppose that n independent observations of Y are available, and the mean is avg(Y). The Chernoff Bound states that with probability 1-delta, the true mean of Y is at least avg(Y)-e, where $$e = \sqrt{\frac{R^2 \ln\left(\frac{1}{delta}\right)}{2n}}.$$

For example, assume that the domain of a random variable is 1 and avg(Y) is the mean of 10,000 samples of the random variable. Then, the true value of the random variable is at least avg(Y)-0.0215 with 99.99% confidence. Similarly, with probability 1-delta, the expected value of variable Y is at most avg(Y)+e. This provides the opportunity to estimate the range of the significance of each pattern from a set of samples.

Given a set of sample data and a threshold min_sig, with probability 1-delta, a pattern P is significant if sig_s(P) >min_sig+e and is insignificant with probability 1-delta if sig_s(P)<min_sig-e, where sig_s(P) is the significance of the pattern in the sample data. Those patterns (referred to as ambiguous patterns) whose significances in the sample are between min_sig-e and min_sig+e remain undecided and need further examination.

Because the sample size is usually limited by the memory capacity and the distribution-independent nature of Chernoff Bound provides a very conservative estimation, the number of ambiguous patterns may be very large. According to the Apriori property, if a pattern does not satisfy the user-specified significance threshold, any of its superpatterns will not satisfy, and hence need not be examined. If a pattern satisfies the threshold, all of its subpatterns will also satisfy and need not be examined. Hence, the order of examining ambiguous patterns provides for computational efficiency.

An ordered pruning is therefore provided to conduct the examination of these ambiguous patterns in an orderly manner according to the pruning power each ambiguous pattern may provide. The ambiguous pattern with the most pruning power is chosen first as the candidate pattern for evaluation. A greedy algorithm can be developed to repeatedly choose the pattern with the most pruning power among the remaining ambiguous patterns until the memory is filled up.

A scan of the data is then performed to compute the significances of this set of patterns and the result is used to prune the space of ambiguous patterns. This iterative process continues until the remaining set of ambiguous patterns can be held all together in memory. Another scan of the data is sufficient to finalize the set of significant patterns. As a result, the expected number of scans through the data is minimized. In most cases, a couple (e.g., 1–5) of scans of the data are sufficient.

The present invention provides a sampling-based method which is devised to efficiently mine long patterns that satisfy a user-specified significance threshold. The Chernoff Bound is employed to estimate the set of ambiguous patterns with very high confidence. Instead of using a level-wise search, an ordered pruning is performed on the set of ambiguous patterns so that the expected number of passes through the dataset is minimized.

It should be understood that the elements shown in FIGS. 1–6 may be implemented in various forms of hardware, software or combinations thereof. Preferably, these elements are implemented in software on one or more appropriately programmed general purpose digital computers having a processor and memory and input/output interfaces. The methods and system as depicted in FIGS. 1–6 may be implemented by programming code in one or more software applications.

Referring now to the drawings in which like numerals represent the same or similar elements and initially to FIG. 1, a system/method for mining significant patterns is shown in accordance with the present invention. In block 101, a full scan of the entire dataset is performed. A set of significant items are generated and random samples of data are taken. Then, in block 102, the set of ambiguous patterns are identified based on the sample data. A pattern P is regarded as an ambiguous pattern if P's significance in the sample data is too close to the threshold min_sig to tell whether P would be significant or not with sufficiently high confidence. This set of ambiguous patterns are further verified against the entire dataset in block 103. Further details of these blocks will be described herein below.

Figure 2:
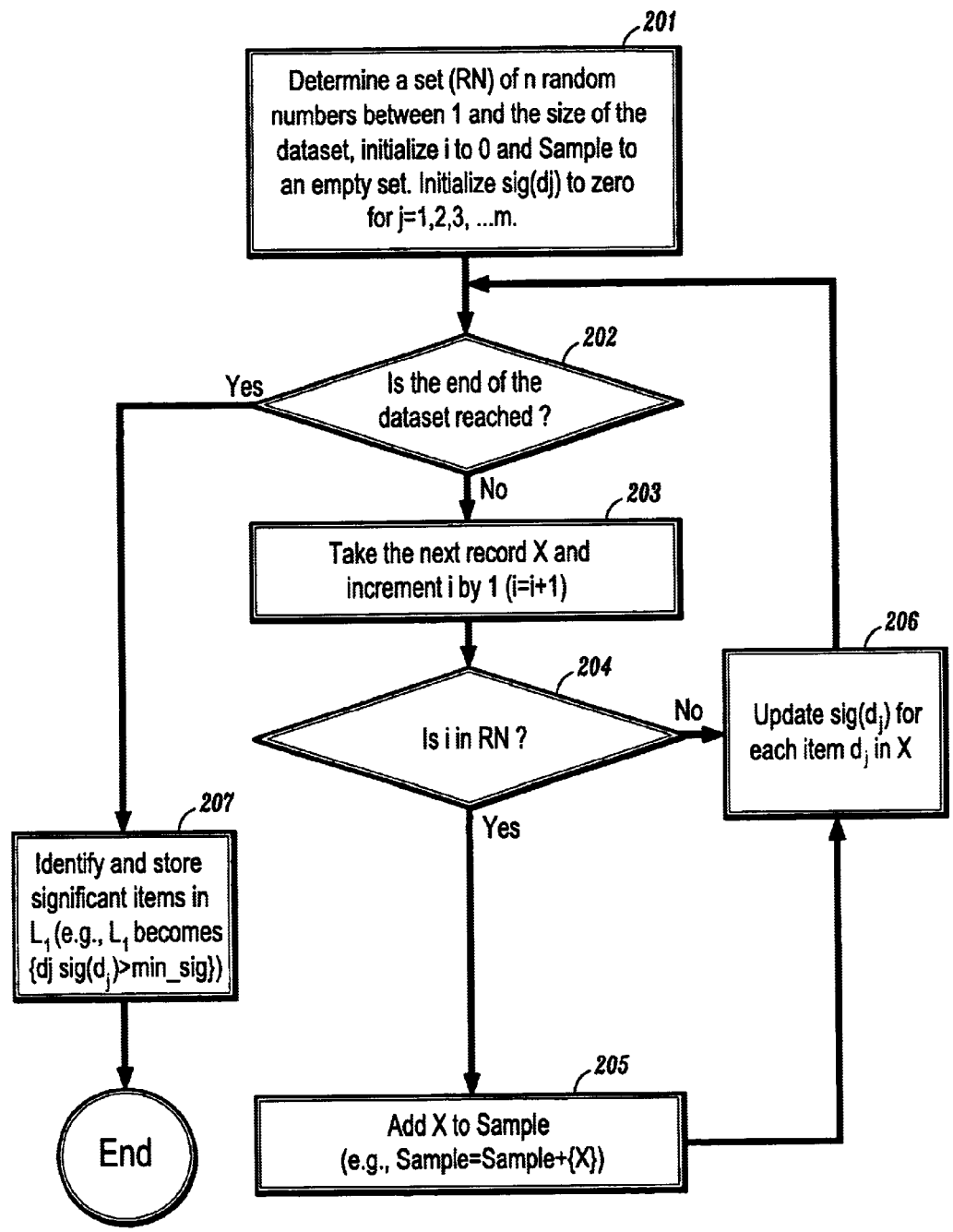
FIG. 2 is a block/flow diagram depicting a system/method for computing a set of significant individual items in the entire dataset and taking a random sample of the data in accordance with the present invention.

Referring to FIG. 2, a method for discovering the set of significant items and taking a random sample of data via a single scan of the dataset, as shown in block 101 of FIG. 1 is illustratively depicted. In block 201, an initialization is performed. A set of n random numbers are drawn between 1 and the size of the dataset and are stored in RN. An index i is set to 0. The set Sample is set to empty and a counter sig($d_j$) is initialized to 0 for each item $d_j$ where j=1, 2, ..., m. The number of samples n is subject to the memory size, i.e., n should be as large as possible given that the sample data can be held in memory all together. A decision block 202 determines whether the end of the dataset is reached. If not, the next data record X is taken and the index i is incremented by 1, in block 203. A test is made in decision block 204 to determine whether the index i is one of the random numbers in RN. If so, X is put in Sample in block 205. In block 206, the significance $sig(d_j)$ is updated for each item appearing in X before looping back to decision block 202. Since the meaningful formula to calculate the significance of a pattern may be different in different applications, this step should be performed accordingly. As a simple example, if the number of occurrences is used as a measure of significance, then $sig(d_j)$<--$sig(d_j)$+1 should be performed in this step. This procedure continues until the end of the dataset is reached. Then, in block 207, the set of significant items are identified and stored in $L_1$.

Figure 3:
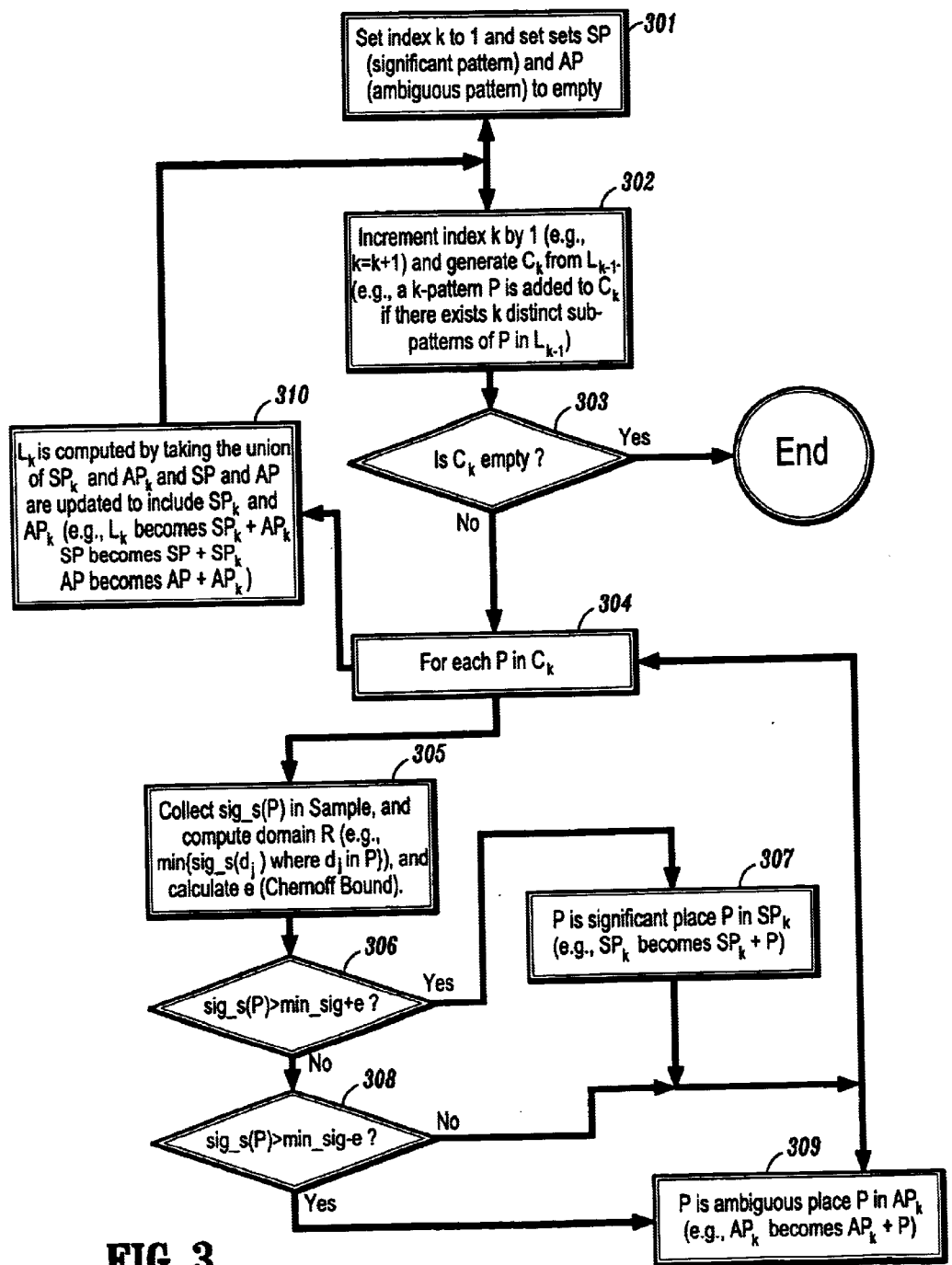
FIG. 3 is a block/flow diagram depicting a system/method for identifying a set of ambiguous patterns based on the sample data in accordance with the present invention.

Referring to FIG. 3, a system/method of identifying the set of ambiguous patterns based on the sample data using Chernoff Bound, as shown in block 102 of FIG. 1 is illustratively depicted. In block 301, an index k is set to 1 and two sets SP and AP are set to empty. SP and AP will be used to store the sets of significant patterns and ambiguous patterns in the sample data. In addition, let $C_k$ and $L_k$ denote the set of generated candidate k-patterns and the set of significant or ambiguous k-patterns in the sample data. In block 302, the index k is incremented by 1 and $C_k$ is generated from $L_{k-1}$ as follows. A k-pattern P is added to $C_k$ if there exists k distinct sub-patterns of P in $L_{k-1}$. A test is then made in decision block 303 to determine whether $C_k$ is empty. If not, the process enter a loop in block 304 where for each pattern P in $C_k$, $sig\_s(P)$ is computed from the sample data and the domain R of $sig(P)$ is computed in block 305. According to the Apriori property, the significance of a pattern is less than or equal to that of any item in this pattern. Thus, the domain of $sig(P)$ can be estimated as the minimum value of the significance of any item in P. Then, the value e is also computed accordingly in block 305 to enable the use of Chernoff Bound. The process then enters a decision block 306 to determine whether $sig\_s(P)$ is greater than $min\_sig+e$. If so, P is significant and is put in $SP_k$ in block 307. Otherwise, another test is made to determine whether $sig\_s(P)$ is greater than $min\_sig-e$ in decision block 308. If so, P is considered an ambiguous pattern and is put in $AP_k$ in block 309. The process then loops back to block 304. After all patterns in $C_k$ have been examined, the process enters a function block 310 where $L_k$ is computed by taking the union of $SP_k$ and $AP_k$, and SP and AP are updated to include $SP_k$ and $AP_k$, respectively.

Figure 4:
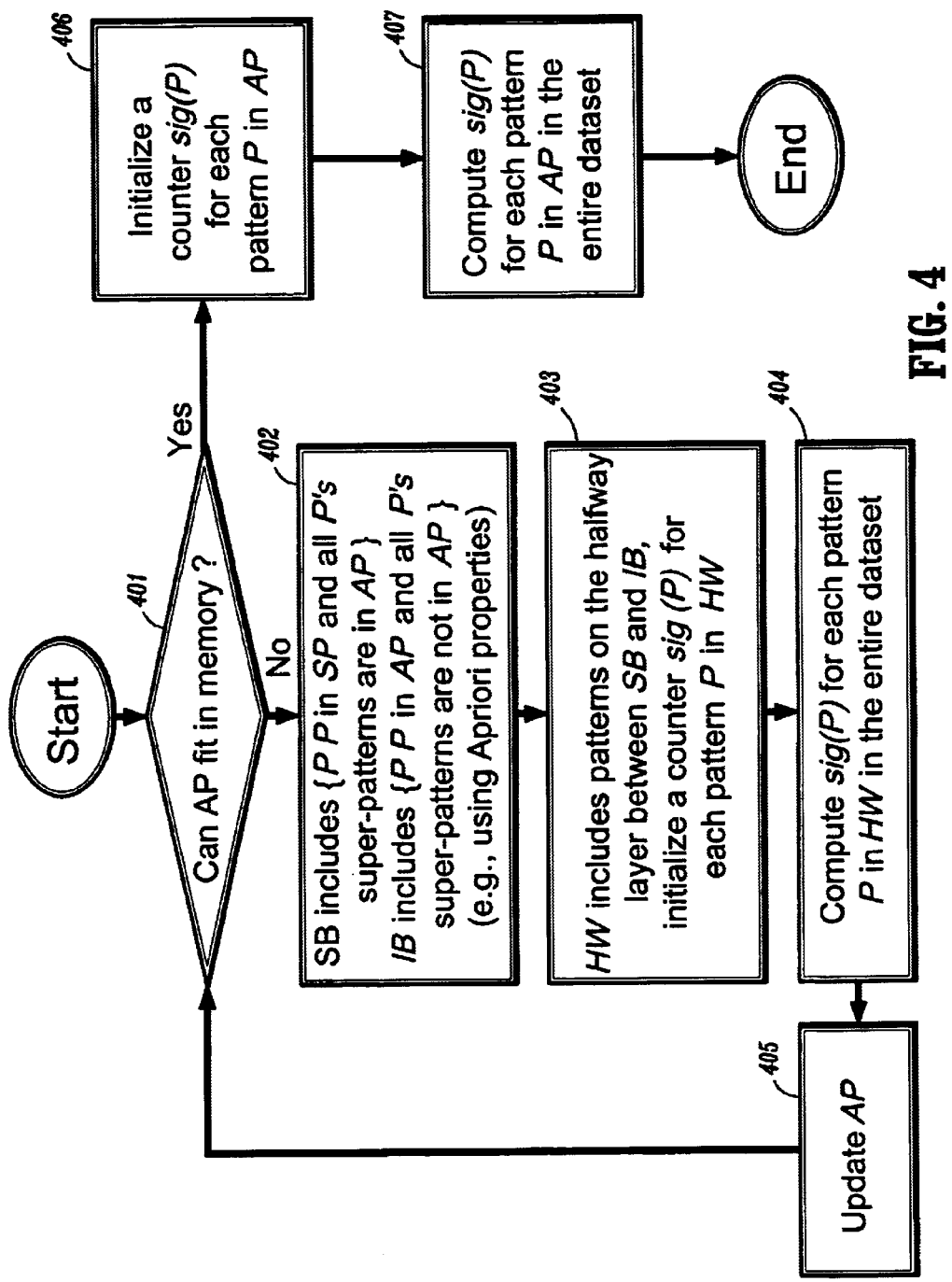
FIG. 4 is a block/flow diagram depicting a system/method for verifying the ambiguous patterns via ordered pruning in accordance with the present invention.

Referring to FIG. 4, a system/method for verifying the set of ambiguous patterns AP against the entire dataset via ordered pruning is shown for block 103 of FIG. 1. The process begins with a test in decision block 401 to determine whether the memory can hold all counters for the set of ambiguous patterns. If not, the set of patterns in SP, whose super-patterns are all in AP (i.e., not in SP) are identified and stored in SB in function block 402. Similarly, the set of patterns in AP, whose super-patterns are all not in AP are identified and stored in IB. These two sets of patterns act as the "floor" and the "ceiling" of the space occupied by ambiguous patterns in the pattern lattice. Then, in block 403, the set of patterns on a halfway (HW) layer between SB and IB (i.e., halfway between the "ceiling" and "floor") are computed and counters for these ambiguous patterns are initialized in memory.

In block 404, the entire dataset is scanned to compute $sig(P)$ for each halfway pattern P and the result is used to update AP in block 405 as follows. For each halfway pattern P, if $sig(P) \geq min\_sig$, then P and all P's sub-patterns are labeled as significant patterns and removed from AP; otherwise, P and all P's super-patterns are labeled as insignificant patterns and removed from AP. The process then loops back to decision block 401. If the memory is sufficient to hold counters for all patterns in AP, then a counter $sig(P)$ is initialized for each pattern P in AP in block 406, and the entire dataset is scanned to compute $sig(P)$ in block 407.

The halfway layer is preferable since the patterns on the halfway layer can provide the most pruning effect, and the result can slash the space of ambiguous patterns by at least half. Other intermediate layers may also be employed and are contemplated by the present invention.

Figure 5:
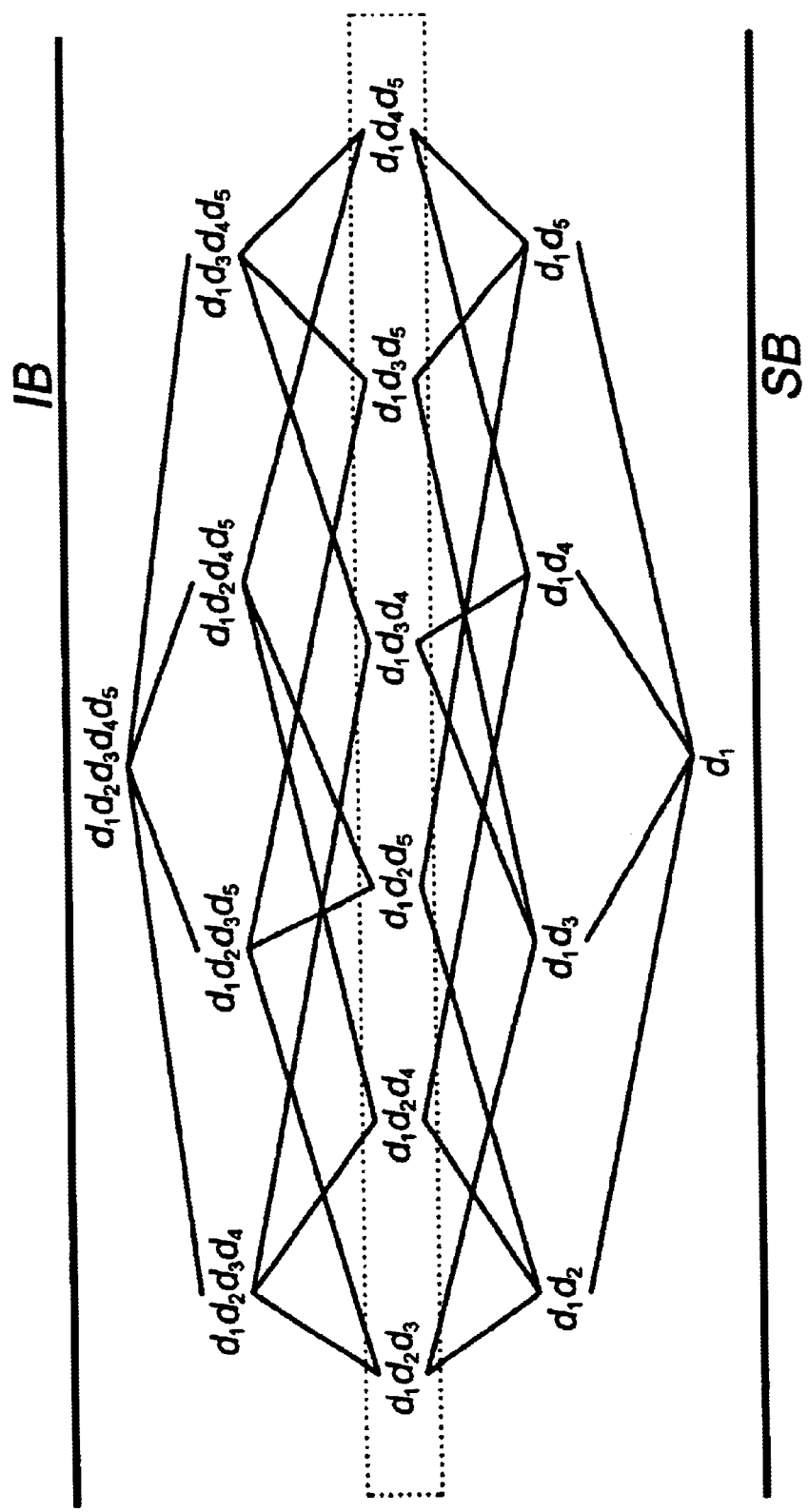
FIG. 5 is an example of space occupied by ambiguous patterns in accordance with the present invention.
Figure 6:
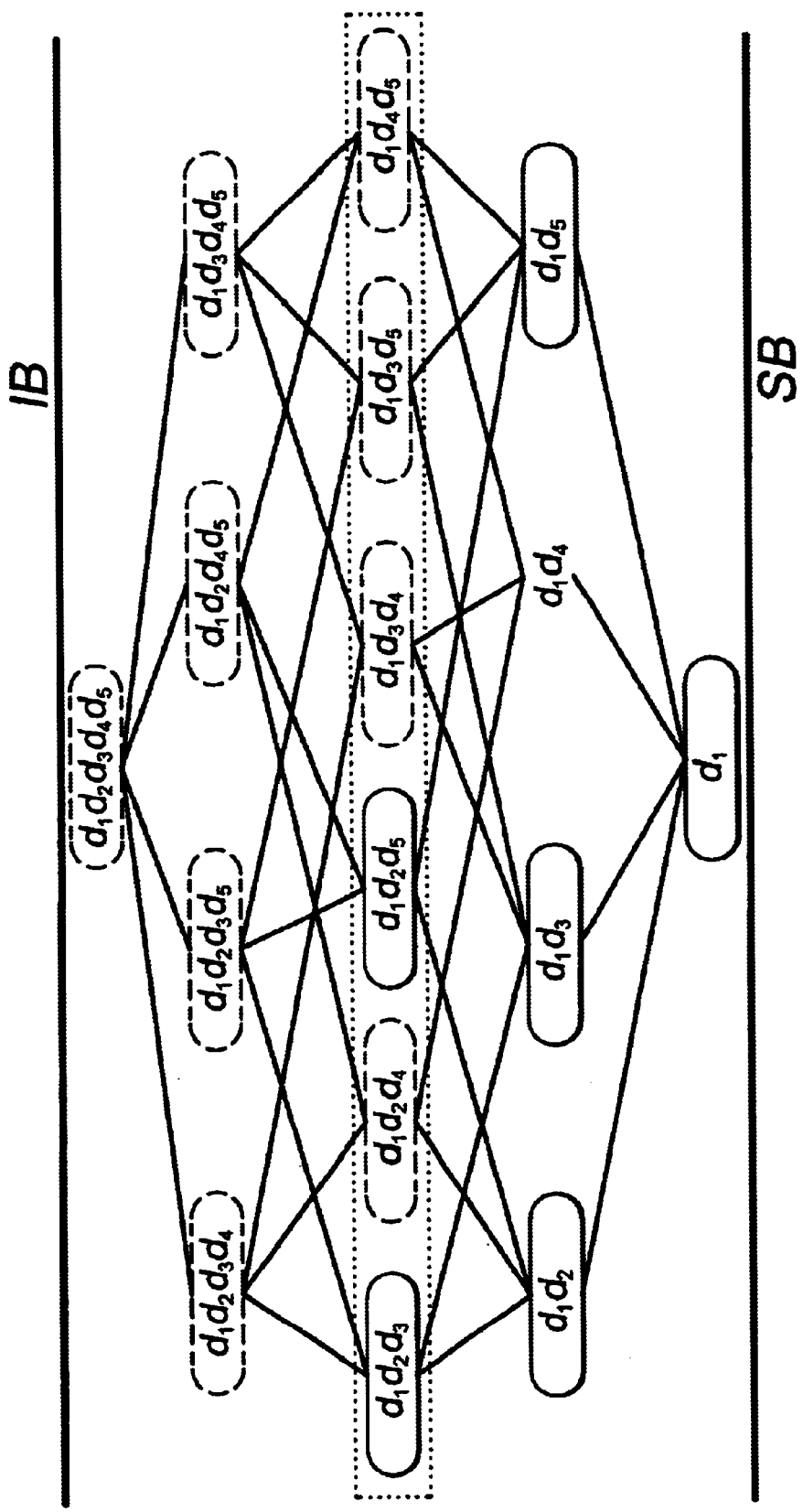
FIG. 6 is a diagram of the pruning effect rendered by the ordered pruning in accordance with the present invention.

Referring to FIG. 5, an example is shown for pruning patterns in accordance with the present invention. A pattern $d_1$ is in SP and the pattern $d_1d_2d_3d_4d_5$ is in AP. Patterns $d_1d_2d_3$, $d_1d_2d_4$, $d_1d_2d_5$, $d_1d_3d_4$, $d_1d_3d_5$, and $d_1d_4d_5$ are halfway patterns between $d_1$ and $d_1d_2d_3d_4d_5$. If a halfway pattern turns out to be significant, then all of its sub-patterns are significant. Otherwise, the pattern is insignificant, and all of its super-patterns are insignificant as well. SP or AP would collapse to the halfway layer if these halfway patterns have homogeneous labels (i.e., either all are significant or all are insignificant). In this case, the space of ambiguous patterns is reduced by half. A more interesting scenario is that the halfway patterns have mixed labels (i.e., some of them are significant while the rest are not), which turns out to provide even more pruning effect. Referring to FIG. 6, assume that $d_1d_2d_3$ and $d_1d_2d_5$ are significant (marked with solid circles on the halfway layer) while the remaining patterns (indicated by dashed circles on the halfway layer) are insignificant. By applying the Apriori property, $d_1$, $d_1d_2$, $d_1d_3$, and $d_1d_5$ should also be significant. Similarly, $d_1d_2d_3d_4$, $d_1d_2d_3d_5$, $d_1d_2d_4d_5$, $d_1d_3d_4d_5$, and $d_1d_2d_3d_4d_5$ are all insignificant. Note that only $d_1d_4$ still remains ambiguous.

Challenges are posed to the design of mining algorithms because data sets may be very large (e.g., only a small fraction of the entire data set can be held in memory at once) and patterns may be substantially long (including a large number of items or events). Even with the help of the well-known Apriori property, the traditional level-wise algorithm becomes very slow. According to the present invention, a novel sampling-based approach is provided. Given a random sample of the data, the Chernoff Bound is used to estimate the set of ambiguous patterns whose significances in the sample are very close to a threshold so that there is no sufficient statistical confidence to tell whether the pattern would be significant or not in the entire dataset. An ordered pruning is also provided to conduct the examination of these ambiguous patterns in an orderly manner according to the pruning power each ambiguous pattern may provide. As a result, the expected number of scans through the data is minimized.

Having described preferred embodiments of a system and method for mining long patterns (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for discovering significant patterns from a list of records in a dataset, wherein each record comprises a set of items and each significant pattern includes a subset of items such that a significance of the pattern exceeds a user-specified significance level, the method comprising the steps of:

computing a significance for each item in the list of records to determine significant items;

sampling the records randomly to select a sample portion of the records;

identifying ambiguous patterns based on the sample portion of the records; and verifying the ambiguous patterns against the entire list of records in the dataset, wherein the step of verifying the ambiguous patterns against the entire list of records includes pruning ambiguous patterns by employing an ordered pruning method.

2. The method as recited in claim 1, wherein the step of computing a significance for each item is performed in a single scan of the list of records.

3. The method as recited in claim 1, wherein the step of sampling the records randomly includes choosing a sample size according to a size of available memory space for storing sampled records.

4. The method as recited in claim 1, wherein the step of identifying ambiguous patterns comprises an iterative loop, wherein a kth iteration identifies all ambiguous k-patterns and the method further comprising the steps of:

generating candidate k-patterns;

computing the significance of each candidate k-pattern in the sample portion; and labeling candidate k-patterns as significant, ambiguous, or insignificant according to the significance of each candidate k-pattern in the sample portion.

5. The method as recited in claim 4, wherein the step of labeling candidate k-patterns utilizes a Chernoff Bound.

6. The method as recited in claim 5, wherein a domain of each candidate k-pattern is computed from the significance of each involved item from the list of records of the dataset.

7. The method as recited in claim 1, wherein the ambiguous patterns are pruned to fit together in a same memory space.

8. The method as recited in claim 1, wherein the ordered pruning method comprises an iterative process, wherein each iteration further comprises the steps of:

computing a set of halfway patterns in a space of ambiguous patterns;

determining significances of the halfway patterns in the entire list of records of the dataset; and reducing the space of ambiguous patterns.

9. A program storage device readable by machine, tangibly embodying a program of instructions executable by the machine to perform method steps for discovering significant patterns from a list of records in a dataset, wherein each record comprises a set of items and each significant pattern includes a subset of items such that a significance of the pattern exceeds a user-specified significance level, the method steps comprising:

computing a significance for each item in the list of records to determine significant items;

sampling the records randomly to select a sample portion of the records;

identifying ambiguous patterns based on the sample portion of the records; and verifying the ambiguous patterns against the entire list of records in the dataset, wherein the step of verifying the ambiguous patterns against the entire list of records includes pruning ambiguous patterns by employing an ordered pruning method.

10. The program storage device as recited in claim 9, wherein the step of computing a significance for each item is performed in a single scan of the list of records.

11. The program storage device as recited in claim 9, wherein the step of sampling the records randomly includes choosing a sample size according to a size of available memory space for storing sampled records.

12. The program storage device as recited in claim 9, wherein the step of identifying ambiguous patterns comprises an iterative loop, wherein a kth iteration identifies all ambiguous k-patterns and the method further comprising the steps of:

generating candidate k-patterns;

computing the significance of each candidate k-pattern in the sample portion; and labeling candidate k-patterns as significant, ambiguous, or insignificant according to the significance of each candidate k-pattern in the sample portion.

13. The program storage device as recited in claim 12, wherein the step of labeling candidate k-patterns utilizes a Chernoff Bound.

14. The program storage device as recited in claim 13, wherein a domain of each candidate k-pattern is computed from the significance of each involved item from the list of records of the dataset.

15. The program storage device as recited in claim 9, wherein the ambiguous patterns are pruned to fit together in a same memory space.

16. The program storage device as recited in claim 9, wherein the ordered pruning method comprises an iterative process, wherein each iteration further comprises the steps of:

computing a set of halfway patterns in a space of ambiguous patterns;

determining significances of the halfway patterns in the entire list of records of the dataset; and reducing the space of ambiguous patterns.

17. A system for discovering significant patterns from a list of records of a dataset, comprising:

a memory storage which stores the list of records, each record of the list of records including a set of items and each significant pattern including a subset of items such that the significance of the pattern exceeds a user-specified significance level; and a processor which determines significant items and generates a random sample of the records, the processor identifies sets of ambiguous patterns based on data obtained in the random sample of records and verifies the ambiguous patterns against the entire dataset such that the ambiguous patterns are pruned from the dataset.

18. The system as recited in claim 17, wherein the processor computes a significance for each item in a single scan of the list of records.

19. The system as recited in claim 17, wherein the processor selects a sample size according to a size of available memory space for storing sampled records.

20. The system as recited in claim 17, wherein the processor labels patterns as significant, ambiguous, or insignificant according to the significance of each candidate k-pattern in the random sample of records.

21. The system as recited in claim 20, wherein the processor employs a Chernoff Bound to label candidate k-patterns.

22. The system as recited in claim 20, wherein a domain of each candidate k-pattern is computed from the significance of each involved item from the list of records of the dataset.

23. The system as recited in claim 17, wherein the processor includes an ordered pruning program to verify the ambiguous patterns against the entire list of records.

24. The system as recited in claim 23, wherein the ambiguous patterns are pruned to fit together in a same memory space.

25. The system as recited in claim 23, wherein the ordered pruning program computes a set of halfway patterns in a space of ambiguous patterns, determines significances of the halfway patterns in the entire list of records of the dataset and reduces the space of ambiguous patterns.

* * * * *